United States Patent [19]
Athey et al.

[11] Patent Number: 5,846,744
[45] Date of Patent: Dec. 8, 1998

[54] SENSORS BASED ON POLYMER TRANSFORMATION

[75] Inventors: Dale Athey; Calum J. McNeil; Ronald D. Armstrong, all of Newcastle upon Tyne, United Kingdom; William Henry Mullen, Grayslake, Ill.

[73] Assignee: Cambridge Life Sciences PLC, Ely, United Kingdom

[21] Appl. No.: 549,800

[22] PCT Filed: May 26, 1994

[86] PCT No.: PCT/EP94/01714

§ 371 Date: Jan. 16, 1996

§ 102(e) Date: Jan. 16, 1996

[87] PCT Pub. No.: WO94/28414

PCT Pub. Date: Dec. 8, 1994

[30] Foreign Application Priority Data

May 29, 1993 [GB] United Kingdom .................... 9311206
Dec. 17, 1993 [GB] United Kingdom .................... 9325898

[51] Int. Cl.[6] ................ C12Q 1/00; C12Q 1/68; G01N 33/53
[52] U.S. Cl. .................... 435/7.9; 435/4; 435/6; 435/7.92; 435/18; 435/25; 435/817; 436/37; 436/151; 436/806
[58] Field of Search ............. 435/4, 6, 7.9, 7.92, 435/18, 25, 817; 436/150, 151, 806, 37; 422/82.01; 204/403

[56] References Cited

U.S. PATENT DOCUMENTS

| 3,979,274 | 9/1976 | Newman . | |
|---|---|---|---|
| 4,072,576 | 2/1978 | Arwin et al. | 436/806 |
| 4,352,884 | 10/1982 | Nakashima | 435/180 |
| 4,402,819 | 9/1983 | Rechnitz et al. | 204/418 |
| 4,920,047 | 4/1990 | Giaever et al. | 435/817 |
| 5,028,394 | 7/1991 | Lowel, Jr. et al. | 422/82.01 |
| 5,063,081 | 11/1991 | Cozzette et al. . | |
| 5,516,644 | 5/1996 | Yamauchi | 435/7.9 |
| 5,540,828 | 7/1996 | Yacynych | 204/403 |
| 5,567,301 | 10/1996 | Stetter et al. | 435/817 |

FOREIGN PATENT DOCUMENTS

| 0193154 A2 | 3/1986 | European Pat. Off. ....... G01N 27/30 |
| 0525723 A2 | 2/1993 | European Pat. Off. . |

Primary Examiner—David Saunders
Attorney, Agent, or Firm—Jacobson, Price, Holman & Stern, PLLC

[57] ABSTRACT

A sensor format is based on impedance analysis of polymer coatings of electrodes. A detectable signal is produced by the effect of a reactive or catalytic species at or very near the polymer coated electrode. The reactive or catalytic species directly or indirectly effects a reaction with the polymer layers, whereby the polymer layer becomes porous and thus causes a measurable change in electrical properties of the electrode surface.

18 Claims, 3 Drawing Sheets

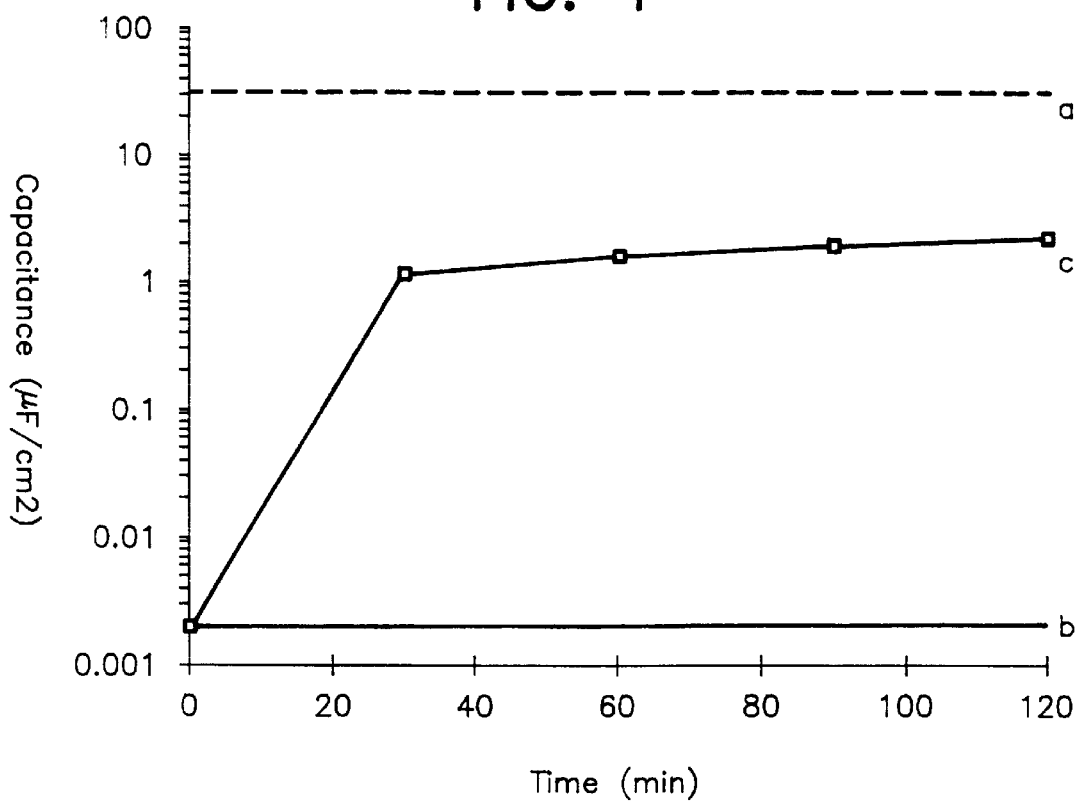
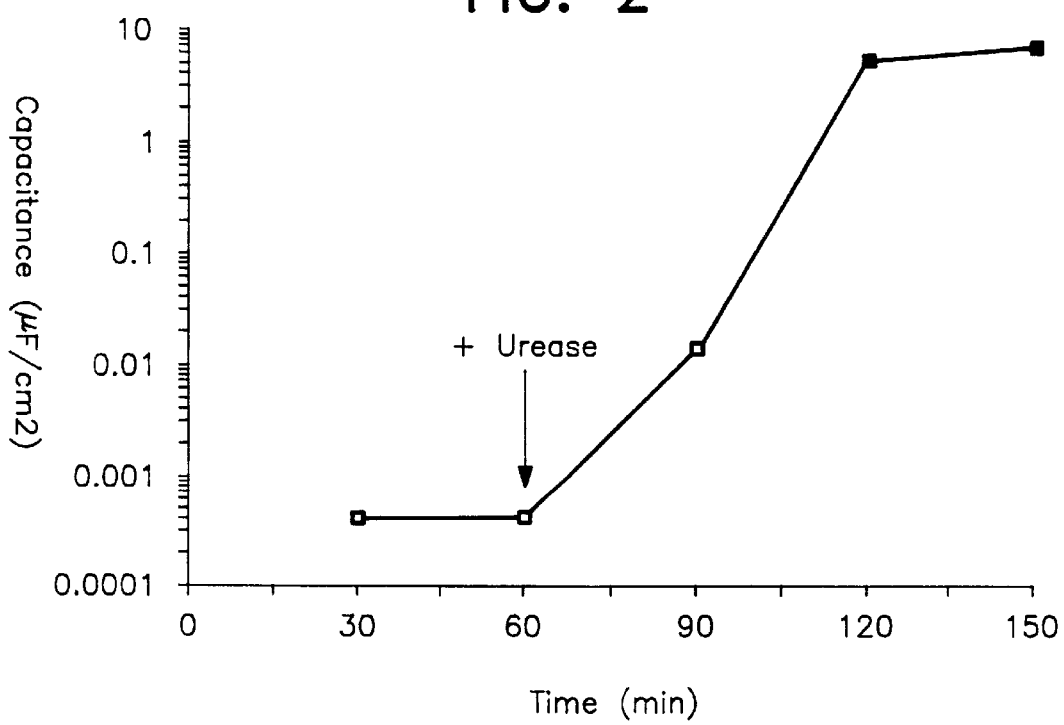

SENSORS BASED ON POLYMER TRANSFORMATION

BACKGROUND OF THE INVENTION

The concept of sensors based on an electrochemical transducer sensitised with a biological moiety, such as an enzyme, is both simple and elegant and offers the prospect of reagentless clinical analysis with minimum sample preparation. The major advantage of this approach for medical use is ease of operation, thus obviating the requirement for trained laboratory personnel to carry out the measurement. This should allow deployment of sensors in decentralised laboratories and facilitate a more rapid return of clinical information to the clinician. The net benefit being an earlier institution of appropriate therapy [Recent Advances in Clinical Chemistry, Vol.3, Alberti, KGMM and Price, CP (eds), Churchill Livingston 1985]. However, in few cases has the concept been translated into practical working devices suitable for near patient testing. Commercially available biosensors based on electrochemical methods are generally either potentiometric or amperometric and for certain clinically important analytes, both of these techniques have drawbacks for biosensor exploitation. In order to circumvent these problems and to produce specific, sensitive techniques suitable for deployment in decentralised laboratories we have demonstrated the feasibility of constructing sensors based on polymer membranes which are modified during operation due to the changes in pH and lead to highly sensitive changes in impedance at underlying electrodes.

Techniques in relation to this type of process have been disclosed for instance, in U.S. Pat. No. 4,352,884 and EP 0 311 768. U.S. Pat. No. 4,352,884 describes a pH electrode having an acrylate copolymer coating for the immobilisation of bioactive materials which was used for the measurement of urea.

This method is only for the immobilisation of bioactive materials such as antigens, antibodies and enzymes and does not play a part in the measurement process. The use of polymer coatings on pH electrodes has a disadvantage of a small dynamic range and poor sensitivity.

EP 0 311 768 describes the modification of a semi-conductive polymer coated on the electrode which becomes more conductive as a result of a homogeneous immunoassay using enzyme conjugates. The method is based on the measurement of resistance which applies a large voltage (500 mV) to the system which may perturb it. The method appears only to cause changes up to 1 order of magnitude and is therefore not as sensitive as the method disclosed in the present invention.

In the present invention, a novel sensor format is described based on the impedance analysis of polymer coatings on electrodes, which require simple fabrication and measurement techniques. The impedance of an electrode is sensitive to a number of factors. Changes in electrode impedance are often caused by changes in double layer capacity. The double layer capacity ($C_{dl}$) arises from the separation at the surface of an electrode between the electronic charges in the metal and the (mobile) ionic charges in the solution in contact with the metal. For a metal (e.g. gold) in contact with a solution of aqueous potassium chloride, this separation is due to the presence of a layer of water molecules on the metal surface. This double layer capacity may be calculated from the standard formula for a parallel plate condenser, $$C_{dl} = e_o e_r A/d \ldots \quad (1)$$

where $e_o$ is the absolute dielectric constant, $e_r$ is the effective dielectric constant of the water layer, A is the electrode area and d is the diameter of a water molecule.

If instead of a layer of water molecules, there is an insulating polymer layer between the metal and the aqueous solution, equation (1) still holds, but d represents the thickness of the polymer layer.

It has now been found that the production of minute imperfections in such a polymer layer give rise to a dramatic increase in capacity which can easily be measured.

The impedance of an electrode is determined by applying a sinusoidal potential of small peak to peak amplitude (typically <10 mV) to the electrode and measuring the resultant sinusoidal current. The range of frequencies which are employed lie between $10^5$ Hz and $10^{-3}$ Hz. There is generally a phase difference (q) between the potential and current so that the ratio of potential to current is essentially a vector quantity (Z) which has magnitude (|Z|) and direction (q). Impedance measurements are often represented in the complex impedance plane where the two components of the impedance vector (Z' and Z") are plotted against each other with frequency as a parameter.

For the electrode impedance to be well defined, it must be measured under steady state conditions. If the electrode condition is changing, the impedance will only be well defined at frequencies above a frequency which is dependent on the rate of change. In principle, an impedance measurement can be made when a steady state current is flowing due to the oxidation or reduction of a species in the solution.

SUMMARY OF INVENTION

The impedance of an electrode can be changed in many ways. For example, the adsorption of a protein on an electrode will cause the electrode impedance to change. However, in order to be useful as a sensor the change of impedance must be highly specific to the substance being sensed and give high sensitivity.

The current invention relies on the occurrence of an enzymic reaction creating changes in the impedance of the electrode as a result of the partial or complete removal of an insulating polymer film from its surface. Other methods of measuring the results of the polymer transformation can be envisaged, such as the measurement of increased current at a polarised electrode. The enzyme or catalyst produces a product which can react with the polymer, or can directly hydrolyse the polymer membrane.

The said enzymes or catalysts may be bound within or directly to the polymer, be present in the bulk solution or bound to the polymer via an antibody-antigen interaction with an enzyme-labelled conjugate or bound to a porous membrane in close proximity to the polymer coated electrode. The examples should not be construed to be the only possible formats of this system.

A further possible application is to transform the polymer coating by an enzymic reaction which causes a chance in pH which then solubilises the polymer allowing the passage of electrolyte to the underlying electrode resulting in a large change in impedance.

One of many appropriate combinations of an enzyme with a polymer coating is the combination of urease with materials such as those used in enteric coatings for tablets. These coatings work by being insoluble at the low pH of the stomach, but are soluble at the pH in the intestine (pH 6 and above). Examples of such coating materials are cellulose acetate hydrogen phthalate, methyl vinyl ether-maleic anhydride copolymer esters, anionic polymerisates of methacrylic acid and esters of methacrylic acid (Eudragit® of Röhm-Pharma, Darmstadt, Germany). In one particular reaction, urease catalyses the breakdown of urea to ammonia and carbon dioxide according to the following scheme:

$$H_2O + urea \rightarrow 2NH_3 + CO_2$$

$$NH_3 + H_2O \rightarrow NH_4^+ + OH^-$$

The resulting increase of the pH value leads to a solubilisation of said materials.

Another application is to apply a pH sensitive polymer whose permeability is reversibly regulated by pH changes in the outer medium. The polymer, poly 4-vinylpyridine is coated on the electrode surface and when the pH becomes acidic, the permeation to ions is increased which is measured by an increase in capacitance at the electrode. Many enzyme reactions may cause the pH to become acidic. In one particular reaction, glucose oxidase catalyses the breakdown of glucose to gluconolactone and peroxide according to the following scheme:

$$Glucose + O_2 \rightarrow gluconolactone + H_2O_2$$

The permeability of the polymer is reversible and can be re-used many times.

If an antibody is immobilised onto said pH-sensitive polymers, it may capture an urease-labelled conjugate in an immunoassay. The bound urease conjugate then produces a local pH change that leads to the solubilisation of the polymer at the point of conjugate capture. Most unexpectedly, we have found that local solubilisation can occur in solutions where, because of the buffering capacity of the bulk solution, a significant pH change in the solution does not take place.

It is also possible to enhance this method by polarising the working electrode at a potential where reactive species can be produced when the electrode comes into contact with the electrolyte. If an electrode is polarised at −600 mV vs Ag/AgCl no reaction will occur until some small amount of electrolyte comes into contact with the electrode, as the polymer layer is just starting to break down. Oxygen reduction at the electrode surface then produces $OH^-$ which increases the local pH further and accelerates the breakdown of the polymer. This results in considerable amplification of the original signal.

In another instance it is possible to use an $H_2O_2$-producing enzyme such as glucose oxidase in conjunction with the Fenton reaction. This reaction is commonly used in synthetic organic chemistry to hydroxylate aromatics, and works by producing the extremely reactive radical OH.; e.g.

$$H_2O_2 + Fe^{2+} \rightarrow Fe^{3+} + OH^- + HO.$$

The hydroxyl radical is so reactive that it survives only until it encounters an organic species. In this case a polymer coating is chosen which contains structure elements reacting with the HO radicals. The introduction of hydroxyl groups enhances the solubility of the coating giving rise to a significant increase of the double layer capacity.

EXAMPLES

The following examples are provided to further illustrate the present invention. It is to be understood that the examples are for purpose of illustration only and are not intended as a definition of the limits of the invention.

GENERAL MECHANISM

Planar carbon electrodes (1 mm diameter) formed by screen printing were coated with cellulose acetate phthalate (CAP) (Kodak) as follows:

A 70 mg sample of CAP was mixed with 30 mg of diethyl phthalate plasticiser and added to 400 mg of acetone to form a viscous solution. A 5 $\mu$l aliquot of this solution was then placed onto the working electrode and allowed to dry in air at room temperature.

The capacitance of the coated electrodes was measured in 150 mmol $l^{-1}$ sodium chloride, pH4, using a frequency response analyser (Schlumberger) and compared with that of bare carbon electrodes. Coated electrodes were then exposed to 150 mmol $l^{-1}$ sodium chloride, pH 6.5, for 15 minutes and the capacitance re-measured.

| Electrode Conditions | Capacitance ($\mu$F $cm^{-2}$) |
|---|---|
| Bare electrode capacitance | 24.6 |
| Coated electrode capacitance, pH 4 | 0.002 |
| Coated electrode after 15 minutes at pH 6.5 | 0.331 |

Exposure of the coated electrode to a solution at pH 6.5 resulted in a 160 fold increase in the capacitance of the electrode.

Gold rod electrodes (4 mm diameter) were coated with cellulose acetate phthalate (CAP) (Kodak) as follows:

The electrode was dip coated once using a 1:8 w/w CAP/30% diethyl phthalate plasticiser to acetone mixture and allowed to dry for 30 minutes at room temperature.

The capacitance of the coated electrodes was measured in 140 mmol $l^{-1}$ sodium chloride, pH4, using a frequency response analyser (Schlumberger) in a three electrode configuration using a silver/silver chloride reference and gold counter electrode. The capacitance of the coated electrode was measured after 5 minutes and 1 hour. The pH 4 solution was removed from the cell and replaced with pH 6.5, 140 mmol $l^{-1}$ sodium chloride solution and the capacitance measured at 30 minute intervals.

| Electrode conditions | Capacitance ($\mu$F $cm^{-2}$) |
|---|---|
| Uncoated electrode | 12.2 |
| Coated electrode, pH 4, 5 minutes | 0.002 |
| Coated electrode, pH 4, 1 hour | 0.002 |
| Coated electrode, pH 6.5, 30 minutes | 1.176 |
| Coated electrode, pH 6.5, 1 hour | 1.584 |
| Coated electrode, pH 6.5, 1.5 hours | 1.944 |
| Coated electrode, pH 6.5, 2 hours | 2.224 |

These results are represented graphically in FIG. 1.

The $pK_a$ values of enteric coatings, CAP and Eudragit S100 polymers, have been calculated by titration of the solid in aqueous solution against dilute base. As both polymers' pH sensitivity is a direct result of the deprotonation of acid ester groups, the $pK_a$ value corresponds to the breakdown pH of the polymer. The $pK_a$ of CAP is approximately 6.0, and the $pK_a$ of Eudragit S100 approximately 7.0

BREAKDOWN OF CELLULOSE ACETATE PHTHALATE FILM USING UREASE

A gold rod electrode (4 mm diameter) was coated with CAP as previously described and inserted into a glass cell. The buffer solution (1 ml) was EDTA (0.5 mM), sodium chloride (140 mM), urea (16 mM) adjusted to pH 4.8 using hydrochloric acid (0.1M).

Capacitance values were obtained at pH 4.8 after 30 and 60 minutes and then urease (20 μl of a 1 mg ml$^{-1}$ solution) was added and the capacitance measured at 90, 120 and 150 minutes.

| Time (min) | Capacitance (μF cm$^{-2}$) |
|---|---|
| 30 | 0.0004 |
| 60 (urease added) | 0.0004 |
| 90 | 0.0133 |
| 120 | 5.000 |
| 150 | 6.500 |

These results are represented graphically in FIG. 2 and confirm that it is possible to breakdown the CAP polymer film by the use of the enzyme urease causing a change in pH and resulting a a 4 orders of magnitude change in electrode capacitance.

BREAKDOWN OF EUDRAGIT S100 POLYMER USING UREASE.

The gold rod electrodes (4 mm diameter) were dip coated twice using 20% w/w Eudragit S100 (Röhm Pharma) in acetone containing 20% w/w dibutyl phthalate plasticiser and 5% w/w Tween 80 and then placed in an atmosphere saturated with acetone for 15 minutes. The electrodes were then removed and allowed to dry for 30 minutes at room temperature.

The glass cell was used containing 1 ml of buffer solution composing of 0.2 mM EDTA, 0.15M NaCl, pH 5.8 and urea over the range 5–50 mM. Initial capacitance values were obtained and after the addition of urease (0.1 mg ml$^{-1}$). The rate of change in impedance as a function of time was urea concentration dependent. The ratio of time capacitance after 10 minutes to the initial capacitance ($C_f/C_o$) is shown as a function of urea concentration in FIG. 3. This clearly demonstrated that urea can be determined by this method and that large changes in signal are involved.

THRESHOLD/TIME BREAKDOWN OF EUDRAGIT S100 POLYMER DUE TO UREA CONCENTRATION.

Stainless steel discs, 10 mm diameter, were sprayed with Eudragit S100 polymer. The polymer composition was 1.1 g Eudragit S100 (Röhm Pharma) dissolved in 13.7 g acetone. Dibutyl phthalate (0.25 g) and Tween 80 (0.3 g) were then added to the mixture. This was applied to the surface of the stainless steel electrodes using a spray nozzle attached to a compressed air cylinder (20 lbf/in$^2$). The optimum spray conditions proved to be 2 applications of polymer with a 30 minute drying time between coats.

Immunodyne membranes (Pall Biosupport) of 0.38 cm$^2$ were loaded with 5 mg ml$^{-1}$ urease in PBS by applying 50 μl to the surface of the membrane for 16 hours at 4° C. The membranes were washed with 140 mM NaCl, 0.2 mM EDTA solution.

Membranes were placed onto the surface of the polymer coated electrode, a gasket placed over the surface of the membrane/electrode and placed in the electrochemical cell. The cell was filled with 1 ml of 140 mM NaCl, 0.2 mM EDTA, pH 5.8 solution.

Impedance measurements were made over the frequency range 20 kHz to 10 mHz to test the integrity of the polymer film. Once the films had been tested, the experiment was started by adding the appropriate amount of urea. The capacitance was followed with time at a frequency of 20 kHz, until the polymer film had disintegrated.

The results which are shown in FIGS. 4 and 5 clearly demonstrate the basis of a 'threshold' measurement for urea.

POLY (4-VINYL PYRIDINE) (PVP) COATINGS ON ORGANOMETALLIC ELECTRODES

Experiments were performed to test the use of PVP as a polymer coating which would break down at acid pH.

Organometallic gold electrodes were dip coated (×1) with the polymer (as supplied in methanol from Aldrich, Chem Co, UK), the electrodes were then left to dry for 16 hours.

The electrodes were then tested as follows:

Impedance measurements were made over the frequency range 20 kHz to 1 Hz, and capacitance values calculated at 20 kHz. Electrodes were placed in the cell with 0.1M carbonate buffer pH9.6, and an initial capacitance measurement made. A value was then taken after 60 min. Subsequently, the buffer was replaced by 0.2 mM EDTA/140 mM NaCl buffer, pH 5.8. Capacitance measurements were made after 5 min and 30 min. Finally, 0.1M carbonate buffer pH 9.6 was re-introduced into the cell and further capacitance measurements made at 5 min and 30 min.

FIG. 6 clearly shows the pH dependency of the insulating properties of the polymer coating, and the reversible nature of this pH effect.

BIOTIN IMMUNOASSAY BASED ON POLYMER BREAKDOWN

A model experiment was performed to demonstrate the immunoassay principle.

Avidin coated membranes were prepared as follows; A 5×5 cm piece of nitrocellulose was wetted using $H_2O$ and then placed on a piece of Whatman No.1 filter paper, and saturated with 1 ml of 5 mg ml$^{-1}$ avidin solution in PBS, pH 7.4. After 1 h the membrane was rinsed in PBS (phosphate buffered saline) and 10 ml of 0.1% glutaraldehyde in PBS added. After 2 h the membrane was rinsed in water, and PBS.

Membrane discs were then incubated with biotin standards (200 μl, 0 to 100 μg ml$^{-1}$ in PBS pH7.4) and a biotin urease (Biogenesis, UK) conjugate (200 μl, 1/50 dilution in PBS pH 7.4) for 2 h at room temperature. The membranes were then removed, washed in water twice, and 0.2 mM EDTA/140 mM NaCl solution once. The membranes were then placed in the electrochemical cell, over the top of an Eudragit S100 polymer coated stainless steel disc to perform impedance analysis.

The urea concentration was adjusted to 100 mM by the addition of 100 μl 1M urea to the 900 μl NaCl/EDTA solution in the cell, and mixing with a pipette. After addition of urea the impedance was monitored for 1 h, capacitance measurements were made from the impedance values at 20 kHz every 15 min.

| Biotin μml$^{-1}$ | Capacitance (nF) time = 0 | Capacitance (nF) time = 1 hour | δC (nF/h) |
|---|---|---|---|
| 0 | 14.6 | 141.3 | 126 |
| 0.01 | 25.3 | 132.7 | 107 |
| 1 | 13.4 | 52.7 | 39 |
| 100 | 26.8 | 23.3 | 0 |

The electrochemical assay according to this invention can be used in many different formats known to the man skilled in the art.

So it is possible to immobilise in any manner known to the man skilled in the art an antibody at the electrode surface for which the analyte to be measured and an analyte enzyme conjugate or an analyte analogue enzyme conjugate compete.

For a sandwich format a first antibody against the analyte to be measured is immobilised at the electrode surface and a second antibody labelled with an enzyme is present in the solution.

For a competition format, a capture antibody is immobilised on a solid phase and then a sample is added containing labelled and unlabelled antigen which compete for antibody sites on the solid phase. The amount of label revealed is inversely proportional to the amount of antigen in the sample.

In a competition format the solution contains a biotin labelled analyte or a biotin labelled analogue of the analyte. An enzyme conjugate with avidin is also present in the solution or may be added after the capture reaction of the biotin labelled analyte or analyte analogue and the analyte to be measured with the immobilised antibody. Other binding pairs in place of avidin/biotin, e.g. IgG:anti-IgG may be used equally.

It is also possible to use a competitive assay where an analyte or an analogue of the analyte is conjugated with an anti-enzyme antibody. Also present in solution is the analyte to be measured and free enzyme, where the signal generated is inversely proportional to the analyte concentration being measured.

Either a sandwich assay format or competition format can also be used where the solid phase is either a coated tube or microwell plate. In this format, the polymer coated electrode is dipped into the coated tube or microwell where the enzyme conjugate reaction with substrate causes the transformation of the polymer.

In a further format, the competition between the analyte and an enzyme conjugate of the analyte or an analogue of the analyte with an enzyme can be performed in a wick (bibulous layer) or a capillary channel in which an antibody against the analyte is immobilised on the surface. After having passed the wick or capillary channel, the unbound enzyme conjugate of the analyte comes into contact with the electrode where an anti-enzyme antibody is immobilised. The signal generated is proportional to the concentration of analyte present.

DESCRIPTION OF FIGURES

The invention is illustrated by the FIGS. 1 to 6:

FIG. 1 is showing capacitance results from (a) uncoated gold electrode (b) CAP coated gold electrode, pH4.0 and (c) CAP coated gold electrode after immersion in pH6.5 buffer.

FIG. 2 is showing capacitance of CAP coated gold electrode as a function of time and the effect of urease (20 $\mu$L of 1 mg/mL) addition.

Figure 3:
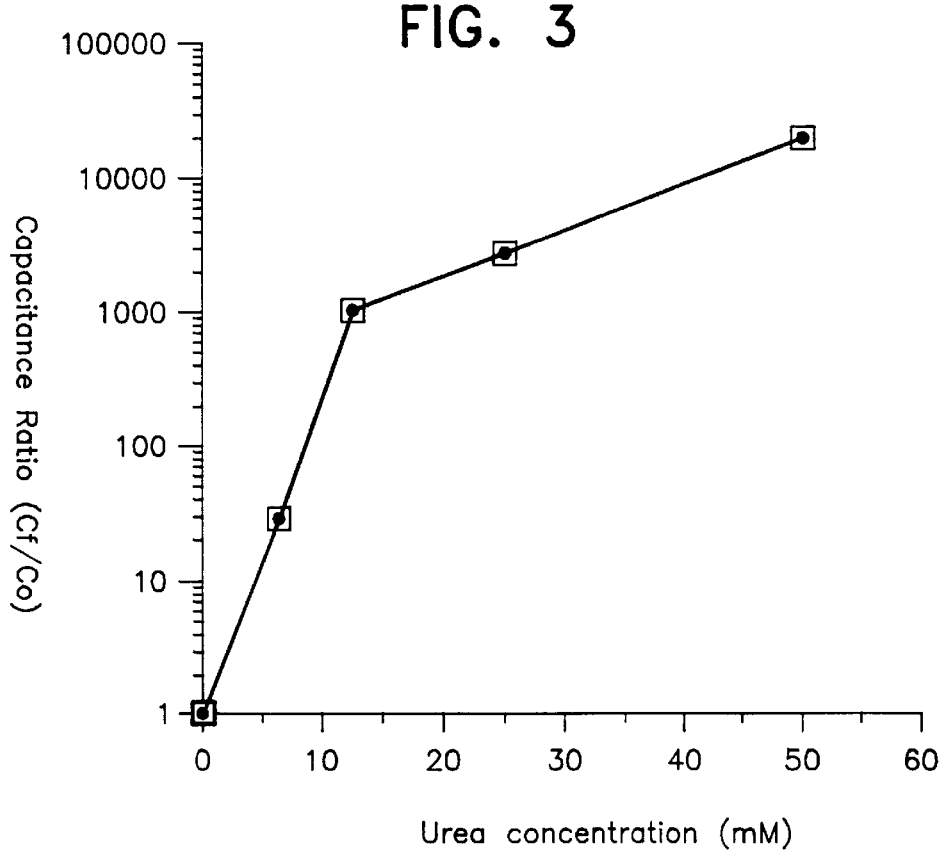
FIG. 3 is showing capacitance change for different analyte (urea) concentration.
Figure 4:
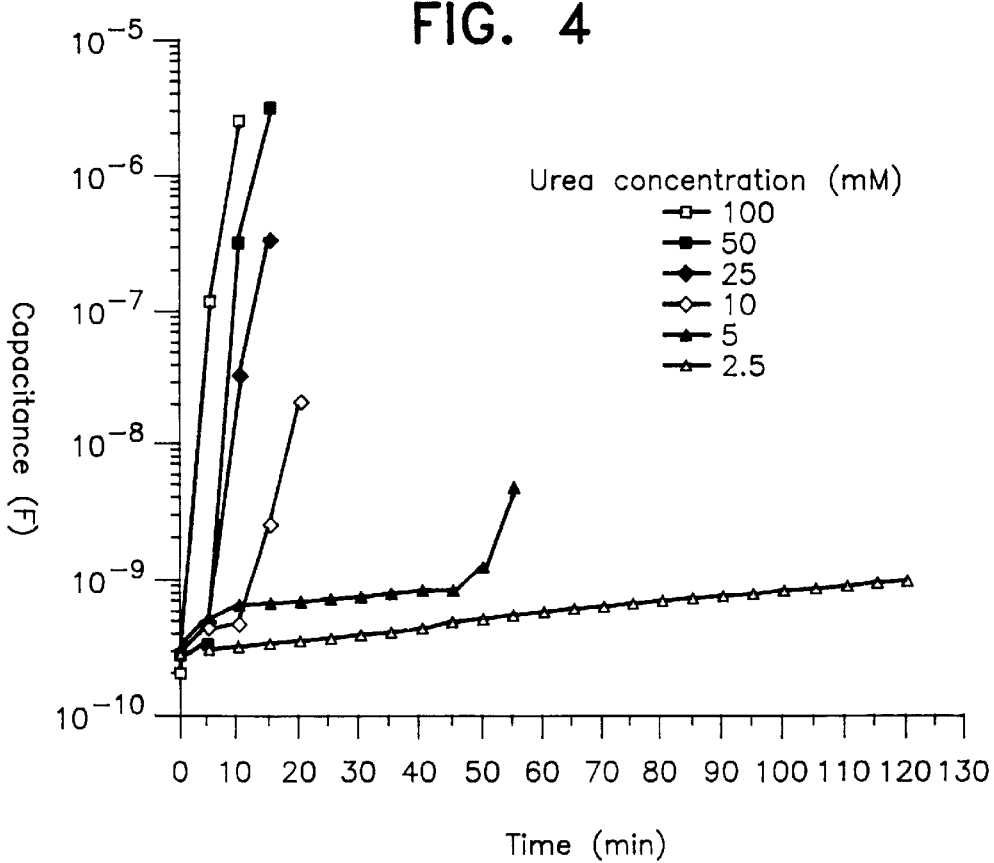
FIGS. 4 and 5 are showing the breakdown of polymer coated electrodes due to analyte (urea) concentration with respect to time.
Figure 5:
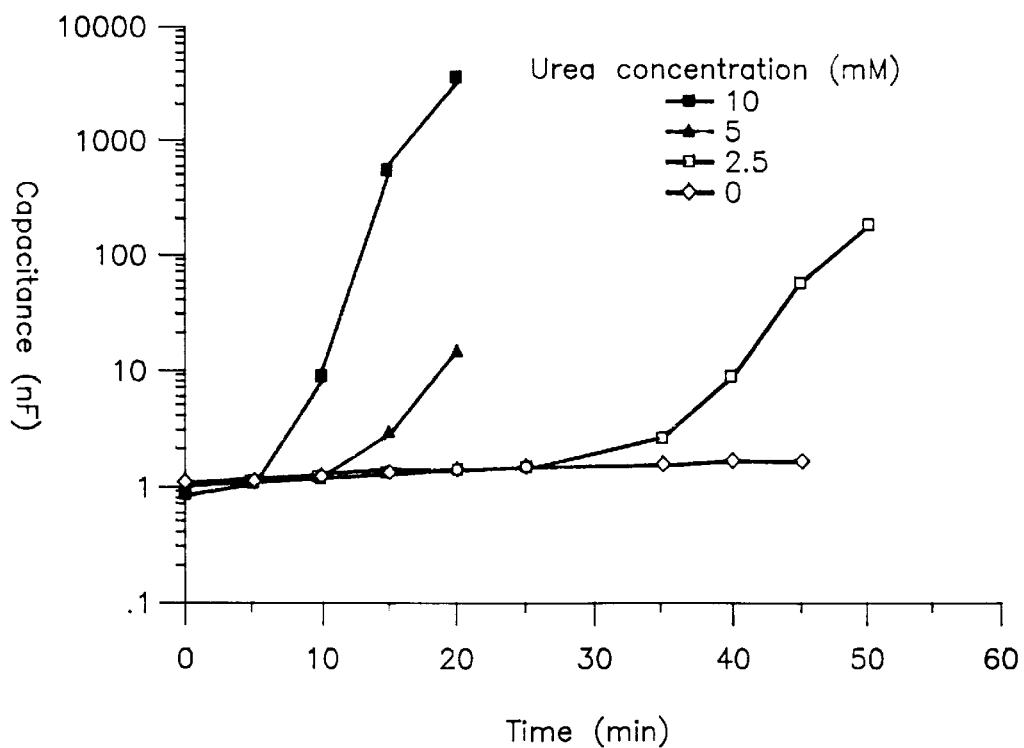
Figure 6:
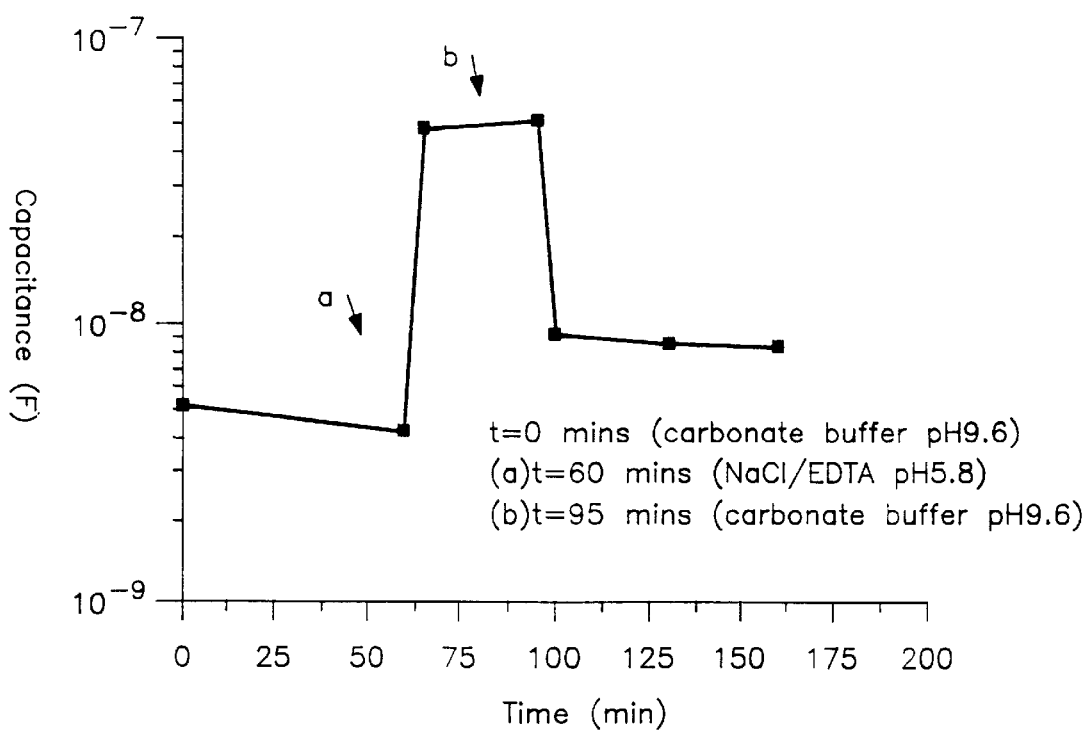
FIG. 6 is showing the effect of solution pH on the capacitance of a poly(4-vinyl pyridine) coated electrode with tine. The electrode at t=0 mins is in carbonate buffer pH9.6. At (a) the electrode is in NaCl/EDTA pH5.8 (t=60 mins) before returning (b) to carbonate buffer pH9.6 (t=95 mins).

We claim:

1. In a method for determining the presence or amounts of an analyte in a sample of assay medium suspected of containing said analyte, said analyte reacting with an enzyme or catalyst to produce an amount of detectible signal which is a function of the amount of analyte in the assay medium, said detectible signal being detected at an electrode in an electrolyte, the improvement wherein:
   (a) the electrode is covered with a thin layer of an electrically insulating polymer that separates the electrode from the electrolyte; and
   (b) the enzyme or catalytic reaction with the said analyte directly or indirectly effects a reaction with the said electrically insulating polymer layer wherein the polymer layer becomes porous or more porous to the electrolyte, causing a measurable change in electrical properties at the electrode surface.

2. A method according to claim 1 where the electrically insulating material is a pH-sensitive polymer and where the enzyme or catalyst reaction causes a change in pH sufficient to increase the permeability of the electrode covering layer.

3. A method according to claim 2 in which the reaction is with an enzyme that reacts to cause a change in pH.

4. A method according to claim 3 in which the enzyme is urease or glucose oxidase.

5. A method according to claim 1 where the sample is aqueous, whole blood, serum, plasma, urine or saliva.

6. A method according to claim 1 in which the electrode is polarised at a potential at which a redox reaction can occur with a constituent of the electrolyte such that breakdown of the polymer layer becomes accelerated once the electrode first becomes exposed to the electrolyte.

7. A method according to claim 1 where the activity of the catalytic species results in the formation of a hydroxyl radical, which is able to react with the polymer layer resulting in an increase in the permeability to electrolyte of said layer.

8. A method according to claim 7 where the catalytic species is a hydrogen peroxide-producing oxidase and the electrolyte contains species able to promote the Fenton reaction.

9. A method according to claim 1 in which the catalytic species is a polymer-degrading enzyme which acts directly on the polymer layer to increase the permeability of the layer.

10. A method according to claim 9 in which the catalytic species is amylase or amyloglucosidase and the dielectric comprises or contains a polysaccharide.

11. A method according to claim 9 in which the catalytic species is an endonuclease and the polymer comprises or contains a nucleic acid.

12. A method according to claim 9 in which the catalytic species is a lipase and the polymer comprises or contains lipid.

13. A method according to claim 1 where the enzyme or catalyst is within the polymer layer.

14. A method according to claim 1 where the enzyme or catalyst is bound to the polymer layer.

15. A method according to claim 1 where the enzyme or catalyst is bound to another support in close proximity to the polymer layer.

16. A method according to claim 15 wherein the other support is composed of a membrane support material.

17. A method according to claim 16 wherein the membrane support material is a nitrocellulose membrane.

18. In an immunoassay method in which an enzyme-antibody or enzyme-antigen conjugate becomes bound at or very near a layer of polymer via a specific immunochemical reaction, the improvement wherein the polymer is an electrically insulating polymer, the layer of polymer covers an electrode and enzyme activity of the conjugate leads to an increased permeability of the polymer layer to electrolyte, measured by a change in capacitance or current passed by the underlying electrode.

* * * * *